United States Patent [19]

Cernosek et al.

[11] Patent Number: 5,763,283
[45] Date of Patent: Jun. 9, 1998

[54] METHOD AND APPARATUS FOR PHASE FOR AND AMPLITUDE DETECTION

[75] Inventors: Richard W. Cernosek, Albuquerque; Gregory C. Frye, Cedar Crest; Stephen J. Martin, Albuquerque, all of N. Mex.

[73] Assignee: Sandia Corporation, Albuquerque, N. Mex.

[21] Appl. No.: 322,119

[22] Filed: Oct. 12, 1994

[51] Int. Cl.$^6$ ............................ G01N 33/00; G01N 29/02
[52] U.S. Cl. ............... 436/183; 73/19.03; 73/23.35; 73/24.01; 73/24.06; 422/83; 422/88; 422/89; 422/98; 436/139; 436/162
[58] Field of Search ................... 436/183, 162, 436/139; 422/69, 83, 88, 89, 98; 364/497, 607; 73/19.03, 23.35, 24.01, 24.06

[56] References Cited

U.S. PATENT DOCUMENTS

| | | | |
|---|---|---|---|
| 4,055,072 | 10/1977 | Fletcher et al. | 73/23 |
| 4,312,228 | 1/1982 | Wohltjen | 73/597 |
| 4,754,645 | 7/1988 | Piche et al. | 73/597 |
| 4,935,692 | 6/1990 | Wakasuge | 324/607 |
| 5,012,668 | 5/1991 | Haworth | 73/24.06 |
| 5,076,094 | 12/1991 | Frye et al. | 73/19.03 |
| 5,235,235 | 8/1993 | Martin et al. | 310/313 D |

OTHER PUBLICATIONS

J.A. Groetsch et al. *Org. Coat. Plast. Chem.* 1981, 45, 394–399.
H. Koizumi et al. *Rev. Sci. Instrum.* 1988, 59, 356–361.
J. Toulouse et al. *Rev. Sci. Instrum.* 1988, 59, 492–495.
C.G. Fox et al. *Anal. Chim. Acto* 1991, 248, 337–345.
T. Endo et al. *Jpn. J. Appl. Phys. Part 1* 1992, 31(*Suppl.* 31–1), 160–162.
H. Goto et al. *Toholcu Draigaku Kagaku Keisoky Kenkyujo Hokoky* 1992 41, 95–106.
H. Wohltjen et al. *Anal. Chem.* 1979, 51, 1458–1464.
H. Wohltjen et al. *Anal. Chem.* 1979, 51, 1465–1470.
S.G. Joshi *J. Acoust. Soc. Am.* 1982, 76, 1872–1878.
E. Gatti et al. *Sens. Actuat.* 1983, 4, 45–54.
G.C. Frye et al., *Appl. Spect. Rev.* 1991, 26, 73–149.
G.C. Frye et al. *Ultrason. Symp.* 1991, 311–316.
R.L. Baer et al. *Ultrason. Symp.* 1991, 321–326.
G.C. Frye et al. *Sens. Mater.* 1991, 2, 187–195.
A.J. Ricco et al. *Sens. Actuat.* 1993, 10B, 123–131.
J.W. Grate et al. *Anal. Chem.* 1993, 65, 1868–1881.
J.W. Grate et al. *Anal. Chem.* 1993, 65, 940A–948A.

*Primary Examiner*—Arlen Soderquist
*Attorney, Agent, or Firm*—Gregory A. Cone

[57] ABSTRACT

A new class of techniques been developed which allow inexpensive application of SAW-type chemical sensor devices while retaining high sensitivity (ppm) to chemical detection. The new techniques do not require that the sensor be part of an oscillatory circuit, allowing large concentrations of, e.g., chemical vapors in air, to be accurately measured without compromising the capacity to measure trace concentrations. Such devices have numerous potential applications in environmental monitoring, from manufacturing environments to environmental restoration.

102 Claims, 10 Drawing Sheets

5,763,283

1

METHOD AND APPARATUS FOR PHASE FOR AND AMPLITUDE DETECTION

This invention was made with Government support under Contract DE-AC04-94DP85000 awarded by the U.S. Department of Energy. The Government has certain rights in the invention.

BACKGROUND

The present invention relates generally to the problem of measuring phase and amplitude changes which occur in electronic devices, in particular sensors. A simple, inexpensive approach toward simultaneous measurement of phase and amplitude requiring only the measurement of voltages has been invented, and will be described, along with a class of embodiments.

Increased concerns about environmental pollution, both in the general environment and in the workplace, have motivated considerable research on high-sensitivity chemical sensors. Other applications, for example in medicine and in drug enforcement, also beckon given adequate sensor capability. As a result, the technology of chemical sensors has made great advances in the past decade.

One of the primary avenues of advancement in this important area of technology has been the development of sensors based on the Surface Acoustic Wave (SAW) phenomenon, in which an electrical transducer integrated onto the surface of a piezoelectric substrate sends acoustic waves along the surface to a similar transducer some distance away on the surface, which converts the acoustic vibrations back into an electrical signal. The distance between transducers provides a precise time delay between the input and output signals.

When a compound adsorbs to the surface of the substrate between the transducers, the acoustic wave velocity is changed, as is the time delay. Many SAW chemical sensors use polymer coatings to increase sensitivity or chemical selectivity to small concentrations of vapors. Such adsorption of vapor on a polymer coating also changes the acoustic wave velocity, again producing a change in time delay. Measurement of this time delay is thus the key to the use of SAW devices as sensors.

SAW-based sensors are generally used as the feedback delay-line element in an oscillator feedback loop. The total time delay in such a loop determines the frequency of oscillation. When an environmental constituent is absorbed on the sensor (either on the SAW oscillator itself or on a secondary element, such as a polymer which chemically reacts with the desired chemical species, in mechanical contact with the SAW oscillator), the time delay characteristic of the SAW device changes slightly. This shifts the frequency of oscillation of the loop. Sensor detection has normally been provided by highly precise frequency counting. Such a method was developed and appears in Wohltjen, U.S. Pat. No. 4,312,228 (1982).

SAW devices, although low-loss elements in themselves, are often coupled to high-loss elements such as polymer layers. As a result, the sensing oscillator has a broad resonance peak, making it difficult to determine the peak frequency of resonance. To overcome the loss of signal in high-loss sensors, a large-gain high-frequency amplifier is inserted in the feedback section of the oscillator loop following the sensor. The attenuation of the signal by the sensor can be determined by measuring the radio-frequency (RF) power in the loop prior to the amplifier stage. This information as well as the absolute frequency measurement of the oscillator loop are thus available for interpretation of the status of the sensor. This technique was developed and appears in Frye and Martin, U.S. Pat. No. 5,076,095 (1991).

The existing technology has two major limitations. First, the precise measurement of frequency requires sophisticated and expensive hardware. Most SAW-based sensors operate at frequencies on the order of 100 MHz, but require monitoring of frequency shifts of 1 to 10 Hz, or 1 part in $10^7$ to $10^8$. Maintaining such precision is routine but expensive, thus limiting the range of practical applications for this class of sensors. It is possible to downconvert the signal to a lower peak frequency (i.e. an intermediate frequency of IF signal) by mixing the signal from the sensor with a signal from another SAW oscillator loop, one that is not sensitive to the chemical being detected. A lower precision frequency measurement may then be made to monitor the SAW-based sensor, involving less expensive monitoring equipment. However, significant care must be taken to insure that the temperature and humidity (primary among a number of influences) to which the reference SAW device is exposed are the same as those of the active chemical sensor. If they are not, spurious frequency shifts will result in the downconverted sensor signal. Such unity of environmental conditions is possible in the laboratory, but not easy to achieve in the field.

The second major class of problems center around the common use, referred to above, of high-loss sensors. When polymer coatings are used to increase chemical sensitivity, their viscoelastic properties make them lossy, especially when their surfaces are coated with yet another layer of the chemical being detected. Under conditions of sufficiently high loss, the feedback oscillator circuit will cease to oscillate, rendering these conventional detection technologies inoperative.

In principle, feedback oscillators having higher gain can be used to force oscillation to continue, at the cost of increased system noise (thus lowering sensitivity) and higher expense. Alternatively, less lossy thinner films of polymer can be used which allow continued oscillation, but mean lower sensitivity and a smaller attenuation response, thus leading to weaker discrimination of the components of the sensor output. A fundamental limitation is indicated here in the use of the dual output technique.

A need exists to directly measure the changes in phase and amplitude of sensing devices whose output is characterized by these parameters. A further need is to allow measurements to be made with lossy sensors in feedback oscillation loops. A further need is for increased sensitivity of detection of sensor response. A still further need is for simpler and less expensive system configurations which allow wider application of modern sensor technology.

SUMMARY

The present invention is intended to address all these needs. The present phase and amplitude detection scheme maintains the capability for dual output parameter monitoring, thus allowing high sensitivity, but eliminates the two major limitations described above. Detection of the phase shift induced by the sensor element is easier to implement than measuring the change in time-delay (frequency), as it requires only voltage measurement. The inherent simplicity of the present system translates into lower cost, making SAW-based chemical sensors and other devices whose basic output is a time delay or a frequency available for much broader application. Phase detection can be carried out with the same precision as frequency counting, since both rely on the same fundamental parameter of the sensor system. However, high-loss sensors will not limit the operation of the present detection scheme, as oscillation need not be maintained for phase measurement to continue. The dynamic range of detection of the present system is limited only by source power level, voltage measurement precision, and system noise. Numerous embodiments and other features, aspects, and advantages of the present invention will become better understood with reference to the following description and appended claims.

BRIEF DESCRIPTION OF THE DRAWINGS

The accompanying drawings, which are incorporated in and form part of the specification, illustrate the present invention and, together with the description, serve to explain the invention.

FIG. 9 shows the measured phase shifts using a detection scheme as in FIG. 2 as a function of vapor concentration for carbon tetrachloride absorbed into a polyisobutylene film on a SAW sensor device. FIG. 9A shows small vapor concentration in parts per million, whereas

FIG. 10 shows time-dependent sensor responses for a trichlorethylene vapor calibration sequence (5, 20, 35, and 50% P/P$_{sat}$ in one minute on/off intervals). FIG. 10A shows the phase shift for the above sequence, while

DESCRIPTION

Figure 1:
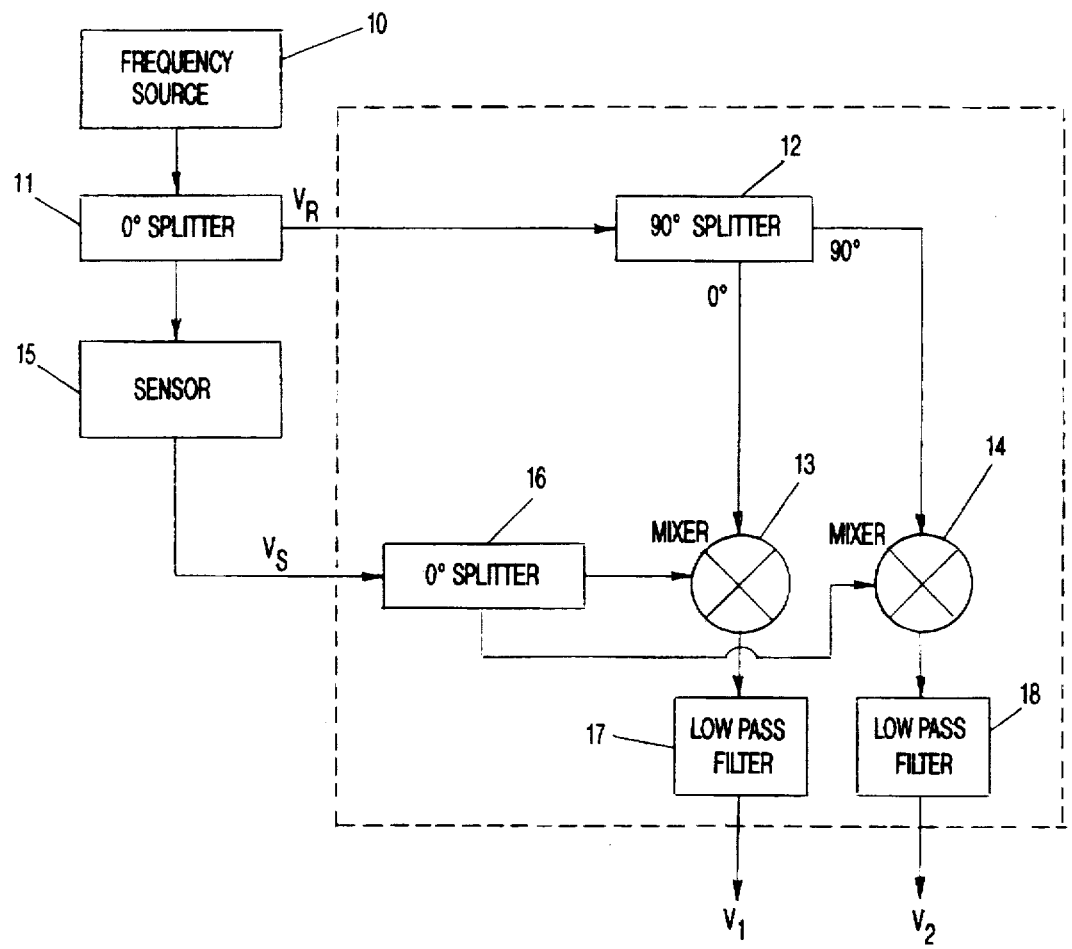
FIG. 1 shows a schematic representation of the basic phase and amplitude detection scheme.

The basic phase and amplitude detection system of the present invention is illustrated in FIG. 1. The following description is based on use with a SAW-type sensor. A stable frequency source 10 (stable meaning that the alterations in measured phase and amplitude which result from slow change in the source frequency and power are less than the desired short- and long-term detection sensitivity of the chemical sensor) generates a continuous signal with a frequency within the peak transmission region of the sensor. The signal is split by nominally 0° splitter 11 into two components having approximately equal amplitude and phase components. These signals are a reference voltage $V_S$, and a sensor voltage $V_s$. The relationships between the amplitudes and phases of these voltages are $$V_R = A_R \cos(\omega t + \phi_R)$$

and $$V_S = A_S \cos(\omega t + \phi_S)$$

where the $\omega t$ term represents the oscillatory nature of the signal, $A_R$ and $A_S$ are the amplitudes of the reference and signal sensor signals and $\phi_R$ and $\phi_S$ are the phase shifts in the reference and sensor arms of the circuit. (Note that these values are also functions of the point in the system where they are being measured. For example, the phase in one arm will change relative to that in the other if the signal line length is changed. Again, such effects are assumed to be smaller than the smallest sensor signal desired to be detected.)

The reference signal $V_R$ is further split into two components nominally 90° out of phase by splitter 12. (This function can be accomplished using either a nominally 90° hybrid splitter or by using a nominally 0° splitter followed by a nominally 90° phase shifter on one leg.) Each of these two signals is sent to the local oscillator (LO) port of separate mixers 13 and 14. The second leg of splitter 12 is sent through sensor 15, and then to nominally 0° splitter 16 where it is split into two nominally equal components. These sensor signal components are sent to the RF ports on mixers 13 and 14. The output signals of mixers 13 and 14 are then sent through low-pass filters 17 and 18, which remove frequency components at the fundamental and harmonic frequencies of frequency source 10. The result is two direct-current (dc) voltages, $V_1$ and $V_2$, whose magnitudes are related by the difference of phase of $V_R$ and $V_S$:

$$V_1 = 0.5 \, A_R A_S \cos \phi$$

and $$V_2 = 0.5 \, A_R A_S \sin \phi$$

where $\phi = \phi_S - \phi_R$. These voltage outputs can be used to solve for the phase and amplitude of the sensor detection system as:

$$\phi = \arctan(V_2/V_1)$$

and $$A_T = 0.5 \, A_R A_S = [V_1^2 + V_2^2]^{0.5}$$

If a reference point for phase and amplitude is established by a single measurement, $\phi_o$ and $A_{to}$, then subsequent measurements will allow the sensor phase and amplitude shifts to be extracted (in the assumption, as made above, that all devices in the sensor detection system save for sensor 15 are nominally zero). The phase shift of the detected sensor signal is $$\Delta \phi = \phi - \phi_o$$

and the amplitude attenuation for a signal propagating through the sensor system is, in dB, $$\Delta A = 20 \log(A_T/A_{to}).$$

Phase detection is possible over $2\pi$ radians; the exact quadrant of the phase vector can be identified by the signs of $V_1$ and $V_2$ in the conventional manner. Maximum phase detection sensitivity occurs when $V_1/V_2$ is near zero. As mentioned in the Background section, the absence of an oscillator feedback loop in the present scheme makes it suitable for use with lossy sensors.

The measurement of phase and amplitude in a sensor system can be implemented exactly as illustrated in FIG. 1. In reality, however, phase and amplitude imbalances are inherent in many of the RF components. Phase imbalances in such components can be greater than 10 degrees while amplitude imbalances can exceed 2 dB, making extraction of the sensor phase and amplitude shifts quite difficult. In addition, reflection of signals at component interfaces often creates enhancement of the above imbalances.

Figure 2:
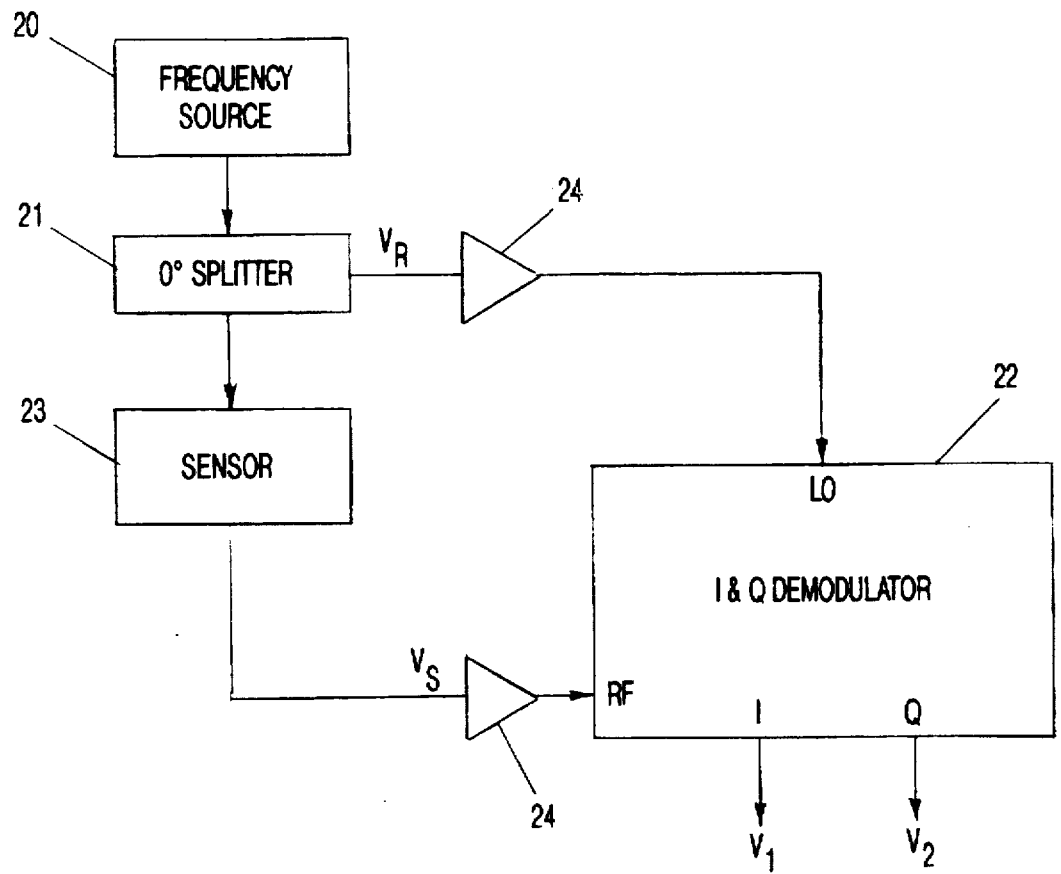
FIG. 2 shows a preferred implementation of the phase and amplitude detection scheme.

An improved implementation of the phase and amplitude detection system appears in FIG. 2. A stable frequency source 20 again sends a signal to a nominally 0° splitter 21. The reference leg of this splitter, however, is now sent to the local oscillator (LO) port of an I (in-phase) and Q (quadrature phase) demodulator 22. (The I & Q demodulator (a commercial component) essentially consists of the components within the dashed box in FIG. 1, but contains extra components for additional balancing and matching.) The sensor leg of splitter 21 is sent through sensor 23, and then to the RF port of the I & Q demodulator 22. Large signal attenuations (many tens of dB) can typically be accommodated at this port. The two output voltages of the I & Q demodulator 22, $V_1$ and $V_2$, are derived from the inphase and quadrature phase mixing of the signals as discussed previously. The resulting system is quite simple, requiring very few electronic components for implementation. The only components needed in addition to those in FIG. 2 are a voltage measuring device (to measure $V_1$ and $V_2$) and a computing means to extract phase and amplitude shifts from those voltages. The scheme shown in FIG. 2 is well-suited to measurement of lossy sensor response as seen in many SAW-based sensor devices.

Figure 3:
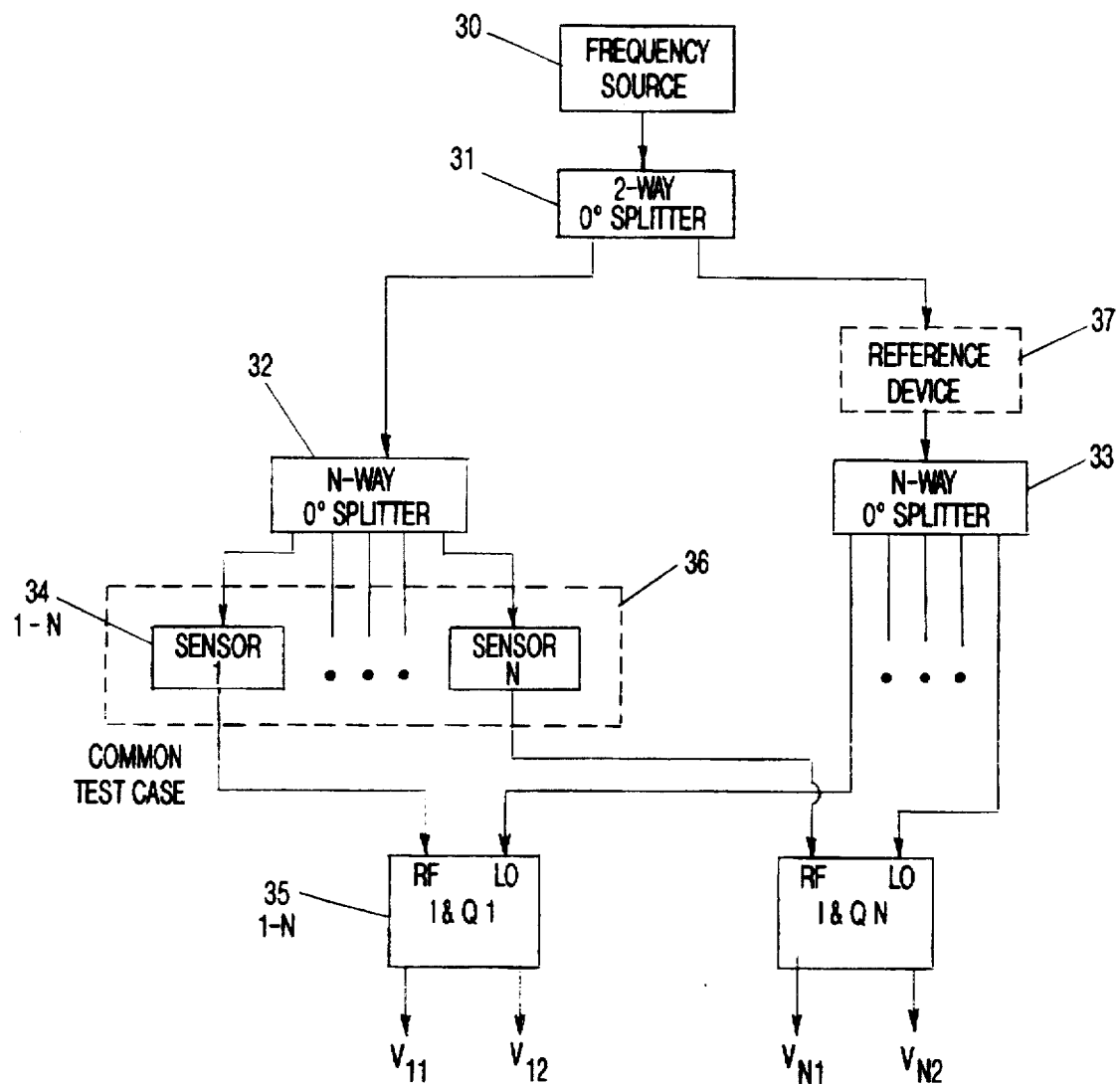
FIG. 3 shows a schematic of a sensor array system that monitors the phase and amplitude shifts in N sensor elements.

In many applications it may be desirable to simultaneously monitor the phase and amplitude shifts generated by a number N of independent sensors. The schematic of FIG. 3 shows an approach toward solving this problem. The signal for the stable frequency source 30 is first split into two nominally equal in-phase signals by 0° splitter 31. Both signal legs of splitter 31 are then split N ways by respective N-way 0° splitters 32 and 33. The set of signal lines coming from splitter 32 are led through N sensors $34_1$–$34_N$, and then separately to the RF inputs of N respective I & Q demodulators $35_1$–$35_N$. The sensors will commonly monitor the same environment, and the phases and amplitudes are sensitive to temperature and other non-chemical environmental changes, so to accommodate these factors the sensors will generally be housed in a common test case 36 (shown as the dotted line around the group of sensors). This need not be done, but simplifies the task of maintaining common environment when this is a priority. The set of signal lines coming from splitter 33 lead separately to the local oscillator inputs of the N I & Q demodulators $35_1$–$35_N$. This circuit yields a 2×N array of signal voltages, which are then processed to determine phase and amplitude information about each of the N sensors 34 as described earlier. Further processing, which may include neural nets or pattern recognition, would allow integration of the sensor data to allow automatic determination of the sensor environment.

Several variations of the multi-sensor scheme of FIG. 3 are useful. It is possible to put a single sensor element 37, similar to sensors $34_1$–$34_N$, but nonsensing (intrinsically or through being sealed off from the local environment) into the signal line leading from splitter 31 to N-way splitter 33. This sensor would then give phase and amplitude shifts due to changes in the non-chemical environment, but would not react to chemical changes, thus acting as a reference device which would allow the outputs of the I & Q demodulators 35 to more purely reflect the chemical changes in the environment. This would also reduce noise due to frequency fluctuations in to frequency source 30, allowing use of a less stable (and thus less expensive) frequency source. (This variation, of course, can also be applied to the apparatus of FIG. 2.)

Other variations would include use of a single 2N in-phase splitter to replace the combined function of splitters 31, 32, and 33. This variation is incompatible with use of a single reference device 37.

Generally, limited source power is available, strong signals are required at the local oscillator inputs of the I & Q demodulators, and highly lossy sensors may result in noisy sensor signals. Overall device operation may thus be improved by amplification, individually or collectively, of the signals. Various boost or buffer amplifiers 24 (see FIG. 2) can be used prior to injection of signals into splitters or into the I & Q demodulators to effect such improvement. Again, this technique may be of use to the device of FIG. 2 if a particularly lossy sensor is being monitored.

There are two potential disadvantages of the basic two-voltage detection scheme described above. These are the need to measure two small voltages with high accuracy and the need to perform some nontrivial mathematics to convert the two voltages into a phase and attenuation response. In principle these disadvantages can easily be overcome by laboratory-grade equipment and large infusions of cash, but they comprise significant obstacles to development of inexpensive sensor systems for more routine application.

Figure 4:
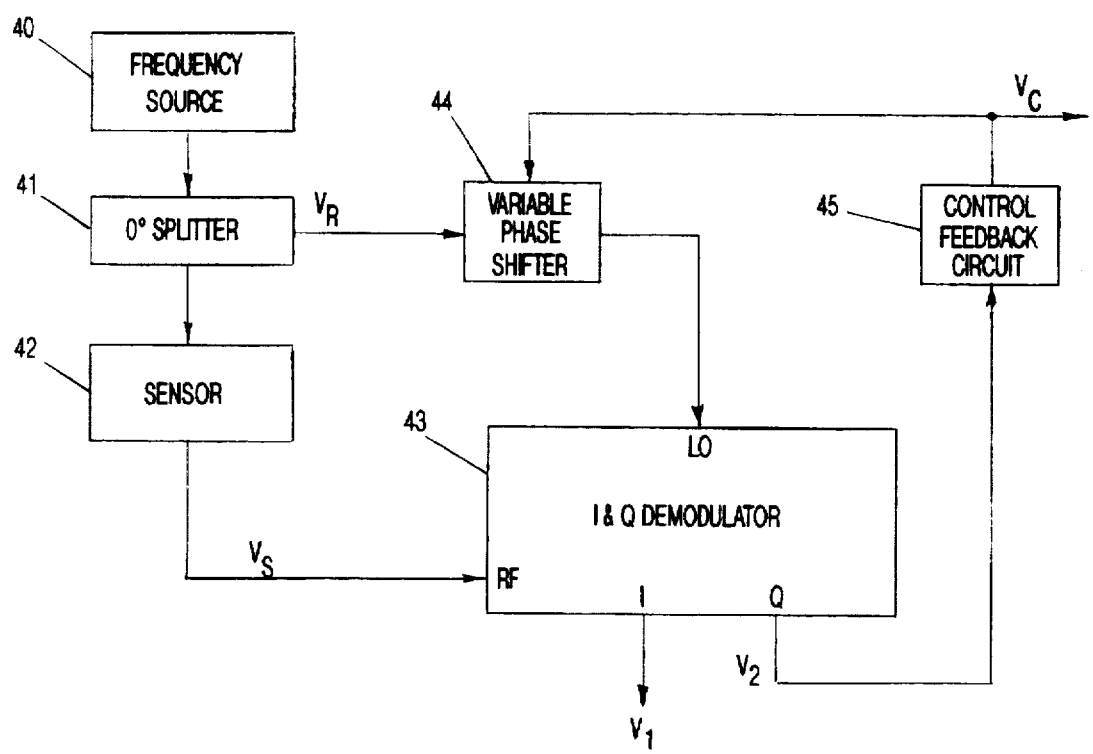
FIG. 4 shows a schematic representation of a phase and amplitude detection scheme which utilizes a phase shifter to adjust for changes in the phase in the signal passing through the acoustic wave sensor in a feedback arrangement to maintain the quadrature phase signal at zero.
Figure 5:
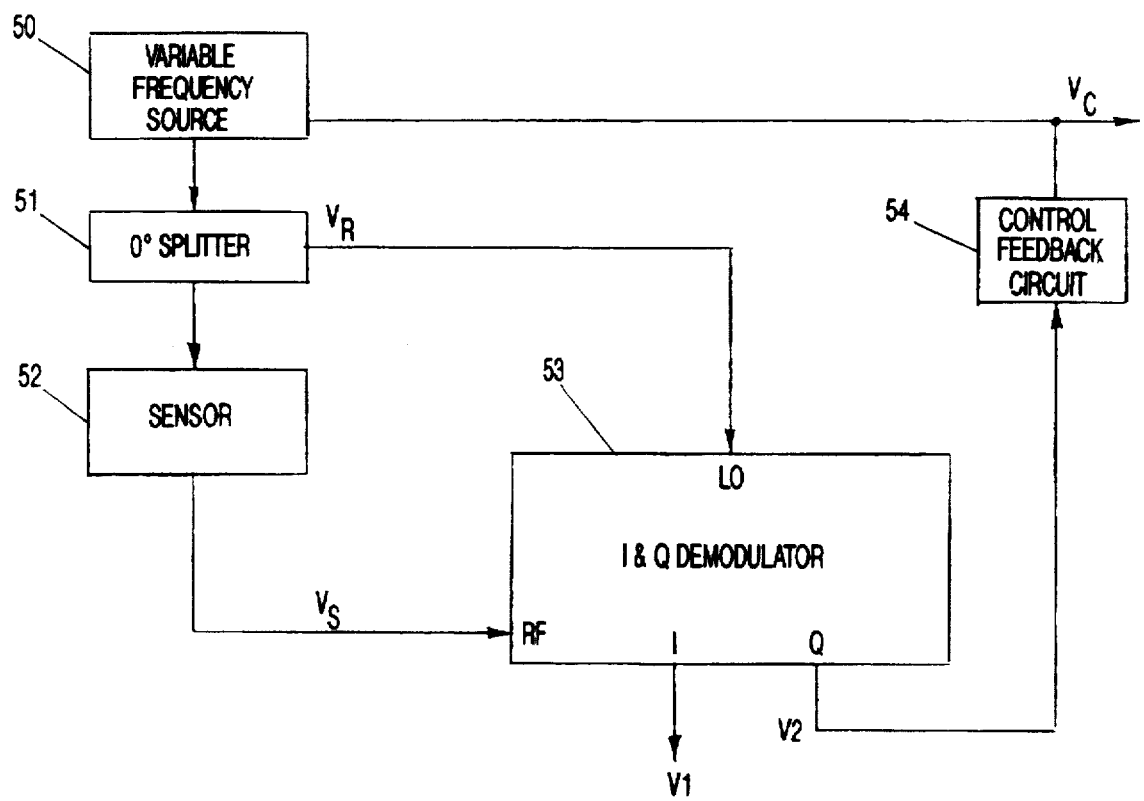
FIG. 5 uses the scheme of FIG. 4, except that the frequency of the variable frequency source is altered to maintain a constant quadrature phase signal.

Two approaches to solving the above problems appear in FIGS. 4 and 5. The basic modification of the earlier scheme is to use a control system (usually a feedback loop) to maintain one of the voltage outputs ($V_2$) of the I & Q demodulator at zero. The control system will provide an output parameter which is a function of the phase shift of the sensor system. With this modification, the other voltage output ($V_1$) is equal to the acoustic amplitude $A_T$ for the sensor circuit. $V_1$ may thus be used to obtain the attenuation response of the sensor directly. $V_1$, is maintained at a maximum level, reducing the requirements on its measurement.

In FIG. 4, the use of a voltage-controlled variable phase shifter 44 is used to adjust the phase of the circuit response to zero using a control voltage $V_c$ produced by the control feedback circuit 45. The control voltage is now related to the phase response of the sensor. If the phase shifter 44 yields a linear phase change with control voltage, the control voltage will be linearly proportional to the phase shift of the sensor. This scheme is also compatible with the multiple sensor scheme of FIG. 3 because the phase in each sensor arm can be controlled separately and the source frequency is not changed.

In FIG. 5 appears a scheme to adjust the frequency to account for changes in sensor phase shift. A variable frequency source 50 is controlled via a control feedback circuit 54 which shifts an output parameter so that output voltage $V_2$ of the I & Q demodulator 53 is kept equal to zero, thus maximizing $V_1$, which is the acoustic amplitude $A_T$. As voltage-controlled oscillators are commercially available and inexpensive, the control parameter would again most likely be a control voltage $V_C$. This configuration mimics a phase-locked loop in that the phase is maintained at a constant level by varying the frequency. Again, measuring $V_C$ allows one to know the frequency shift, and hence the phase shift, which is linearly proportional to frequency shift. If the frequency changes linearly with control voltage, then a simple conversion is possible.

Since the gain of the control circuit in FIGS. 4 and 5 can be varied, the size of the voltage response as a function of phase can be set at any desired value. The circuit can thus be designed so that expected output voltages are large enough to be easily measured using standard voltage measurement electronics (for example, a range of ±5 volts would be common for analog-digital converters). The net effect of this class of implementation is to maximize the voltage used to monitor sensor attenuation ($V_1$), while the magnitude of the voltage used to monitor sensor phase shifts ($V_C$) can be set at a comfortably large value for measurement.

Another possibility is to set the gain of the control feedback circuit so that $V_C$ is a simple multiple of the chemical concentration in the environment to which the sensor is exposed (e.g., 1.0 volts=1000 parts per million of a given chemical). In this way, the chemical calibration coefficient is built into the control feedback circuit so that no complex mathematics is required for data conversion. A simple voltmeter would provide a direct indication of the chemical concentration. It would be useful to include a system, either automated or manually operated, to set the control feedback circuit voltage to zero when no chemical is present. This can be accomplished simply, e.g., by a circuit which offsets the control voltage by a constant value equal to −1 times the value of the non-offset control voltage when no chemical is present, or by a voltage-controlled phase shifter, or by changing the base frequency of the frequency source. This type of modification simplifies the interpretation of the control voltage.

When a zeroing circuit as above is used, this sensor phase and amplitude detection system can be combined with a variable gain voltage measuring device to enable measurement of a wide range of chemical concentrations. When the concentration is low, a high gain setting is used so that the signal is a significant fraction of the measurement range of the voltage measuring system. As the concentration increases, the gain would be turned down so that the control voltage is not larger than the capacity of the voltage measurement system. In this way, both high and low concentration samples could be accurately analyzed using a single measuring system.

Figure 6:
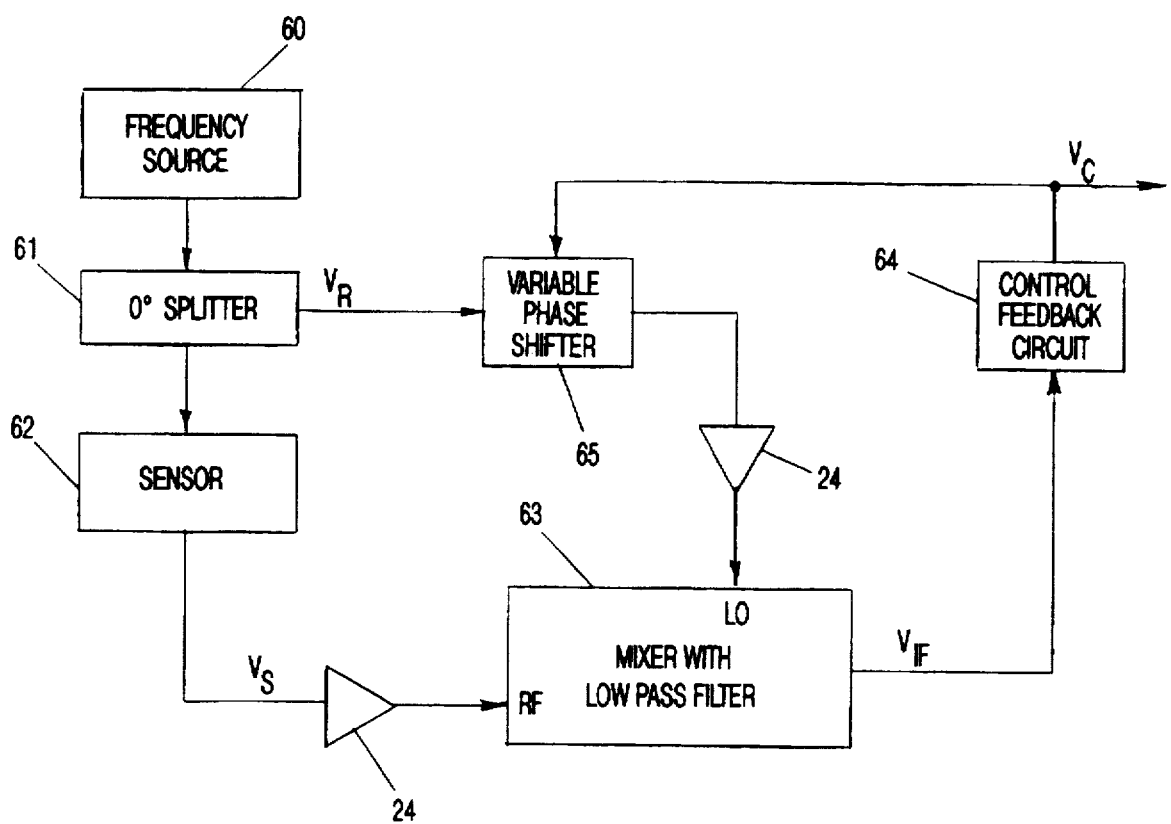
FIG. 6 shows a schematic representation of a simplified version of the apparatus in FIG. 4 suitable for SAW devices having low signal loss.
Figure 7:
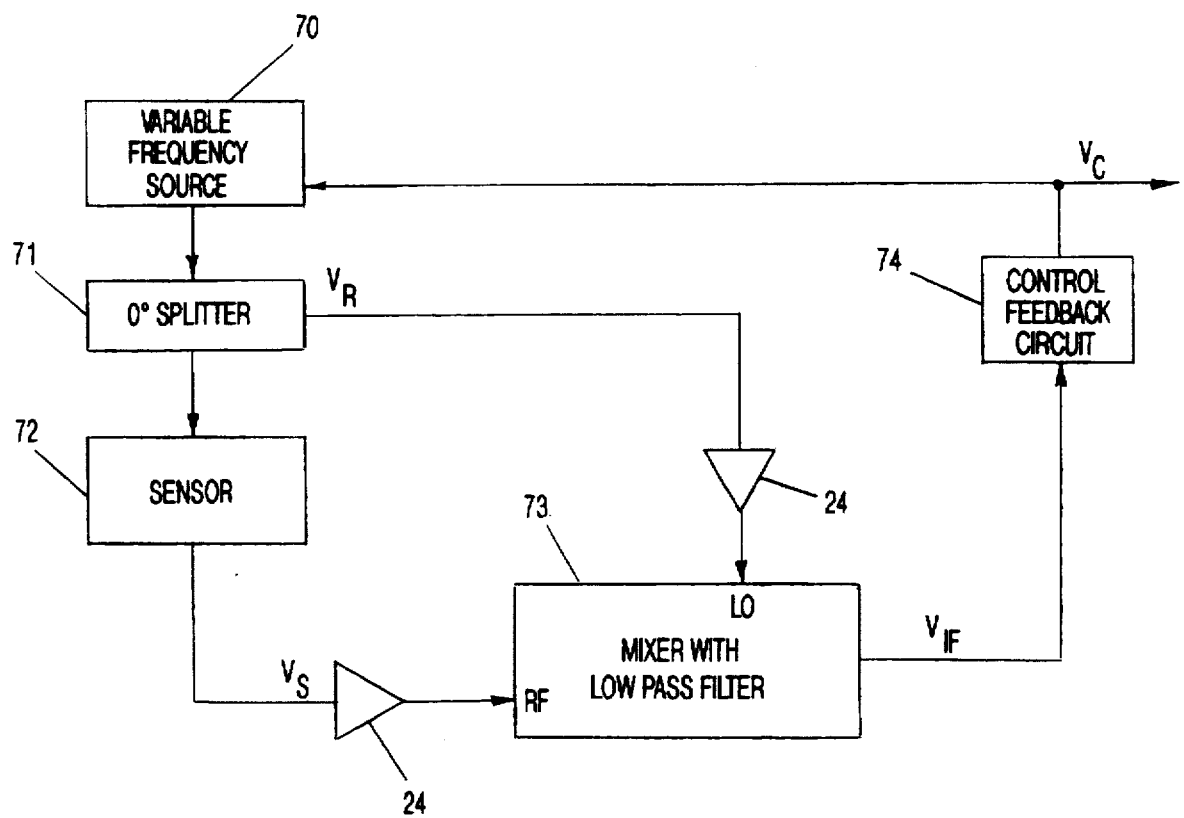
FIG. 7 shows a schematic representation of a simplified version of the apparatus in FIG. 5 suitable for SAW devices having low signal loss.

In some cases, only the sensor phase shift information is required to interpret the sensor response. This could occur if a sensor coating material is used which does not provide a significant attenuation response, such as an elastic film (e.g., porous oxides) or simply a very thin film which does not produce significant attenuation. Another possibility is that the attenuation response may not be distinct enough from the phase shift response to provide additional useful information. In such cases, a simplified version of the controlled feedback systems of FIGS. 4 and 5 can be used as shown in FIGS. 6 and 7. The main difference is that the I & Q demodulator has been replaced with a single mixer and a low-pass filter. In FIG. 6 and 7, various boost or buffer amplifiers 24 can be used if needed to insure adequate signal levels at the LO and RF inputs of the mixer 63. The voltage out of the mixer 63 or 73 is proportional to the RF power levels in the two inputs times the sine of the phase between the two inputs. Once again, the control feedback circuit 64 or 74 is used to maintain this mixed voltage at zero. The control signal (a voltage for example) then allows determination of the sensor phase (or frequency) shift. Since feedback control systems are generally very sensitive to offsets from zero, it may be possible to subject the sensor to lower power levels than when the attenuation response is of interest.

Figure 8:
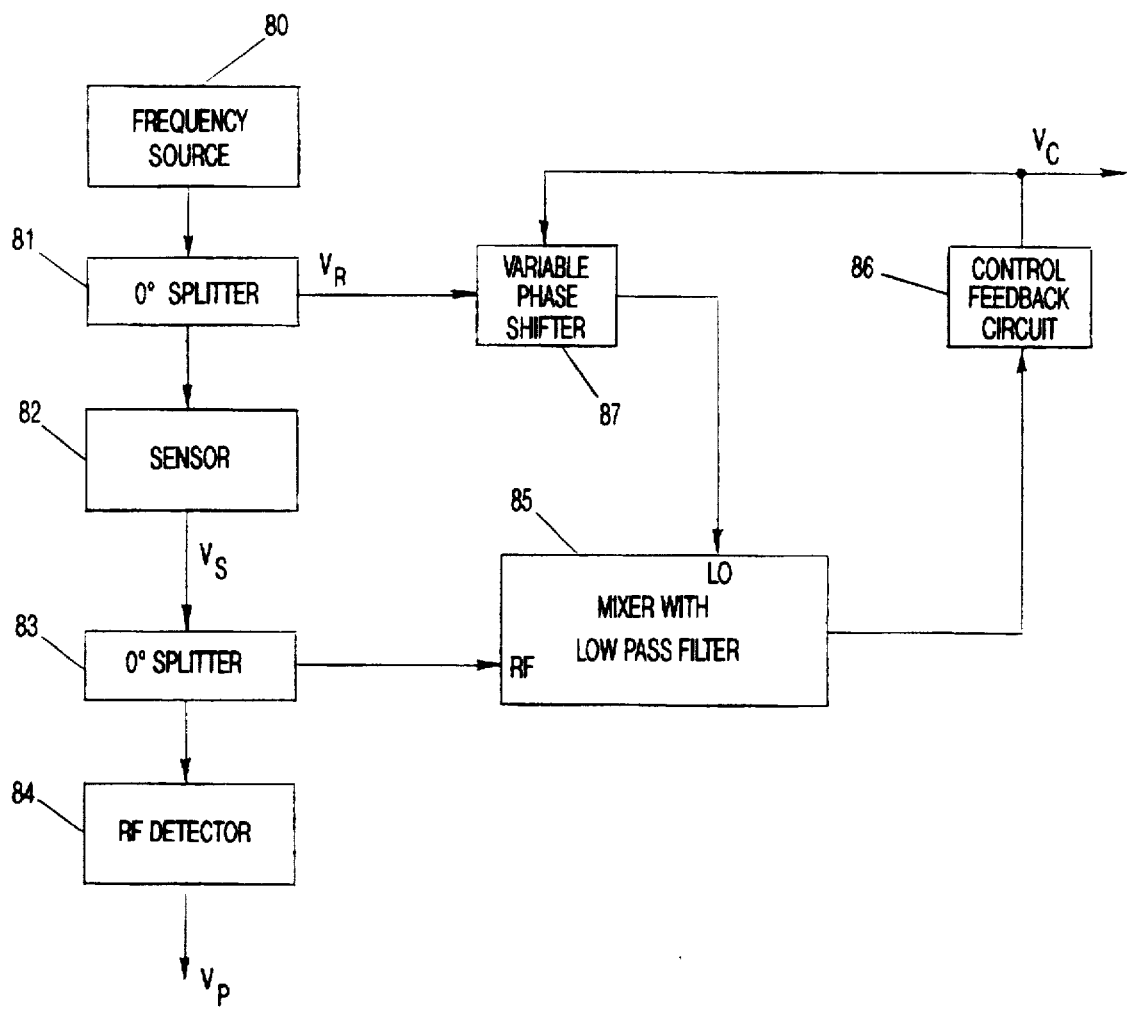
FIG. 8 shows a single mixer configuration which still provides dual output sensing.

Although the single mixer embodiments above will only provide phase information, it is still possible to use such simple components and obtain the attenuation response. This is shown in FIG. 8, where a two-way 0° splitter 83 has been placed in the signal line following the sensor. One output of this splitter goes to the RF input of mixer 85, to drive the feedback loop which provides the control voltage, while the other output goes to an RF power detector to convert the RF power level in this arm to, e.g., a DC voltage $V_P$ which provides the attenuation response.

In SAW chemical sensing, the response time of the sensor is not instantaneous, depending as it does upon the sensor structure (e.g., the polymer film) to become saturated with the environmental vapor before a steady response is obtained. Hence, another parameter which can be of help in identifying species of chemicals is the diffusion time of the vapor or contaminant into the sensor. Measurement of the signal response time provides this information. Since precision voltage measurements can be made rapidly compared to frequency measurements, the new class of sensor amplitude and phase measurement schemes described herein provides a much improved means to measure such diffusion times.

Such rapid monitoring capability can be applied to a fast gas chromatographic system using a SAW detector, increasing the speed of operation greatly. Previous GS-SAW systems have been limited in speed by the need to measure frequency to parts in $10^{7-8}$ or have depended on expensive and environmentally sensitive mixing electronics to reduce frequencies and a very sophisticated and fast frequency counter. The present technique provides rapid monitoring as only voltage measurements need be made. In addition, the three-fold information of phase shift, attenuation, and diffusion time provides additional chemical information about each chemical peak detected.

The basic phase and amplitude detection system shown in FIG. 2 was implemented and demonstrated in several laboratory tests. In the two examples described below, source frequency was in the 95 to 97 MHz range, and source power varied from +13.5 dBm to +17 dBm depending on the test. The I & Q demodulators were obtained from Mini-Circuits, model MIQA-100D -1. The phase and amplitude shifts were obtained by reference to the unperturbed sensor.

EXAMPLE 1

Figure 9A:
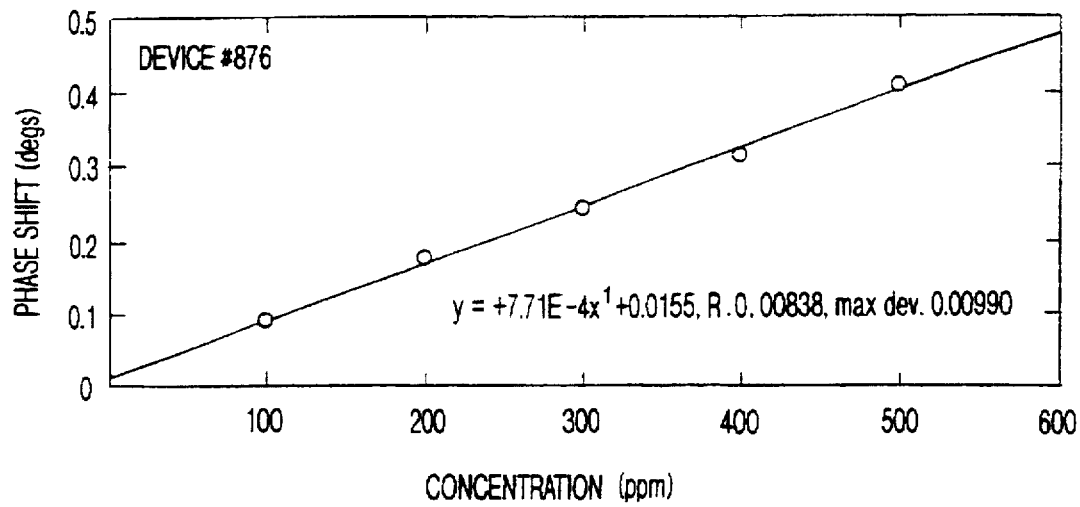
Figure 9B:
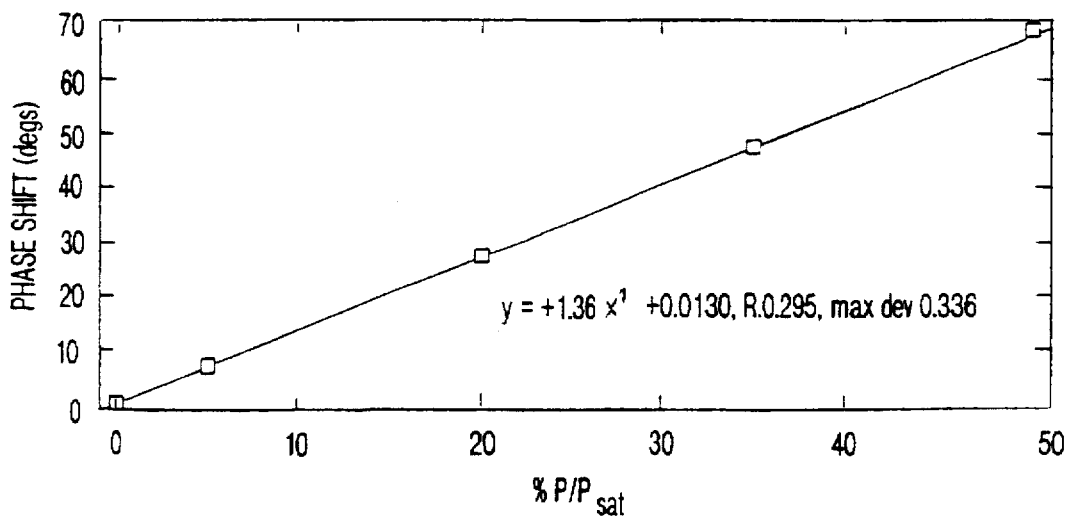
FIG. 9B shows large vapor concentration as saturation relative to the saturation vapor pressure.

A sensor device for carbon tetrachloride in the atmosphere was constructed by layering a polyisobutylene film on a SAW device. The sensor was integrated into a detection system as outlined in FIG. 2, and gas including carbon tetrachloride vapor of known concentration was flowed over the sensor. The two plots in FIG. 9 show the measured phase shifts versus vapor concentration. In FIG. 9A the capability of the system to measure low vapor levels is illustrated. No nonlinear deviation from the expected linear response was found, although a nonzero intercept of 0.0155 degrees of phase shift is suggested by the least-squares fit. (This corresponds to a concentration of 12 ppm, a very low value.) In FIG. 9B the response of the sensor to vapor concentrations on the order of the saturation vapor pressure $P_{sat}$ appears. A linear response was again found.

EXAMPLE 2

Figure 10A:
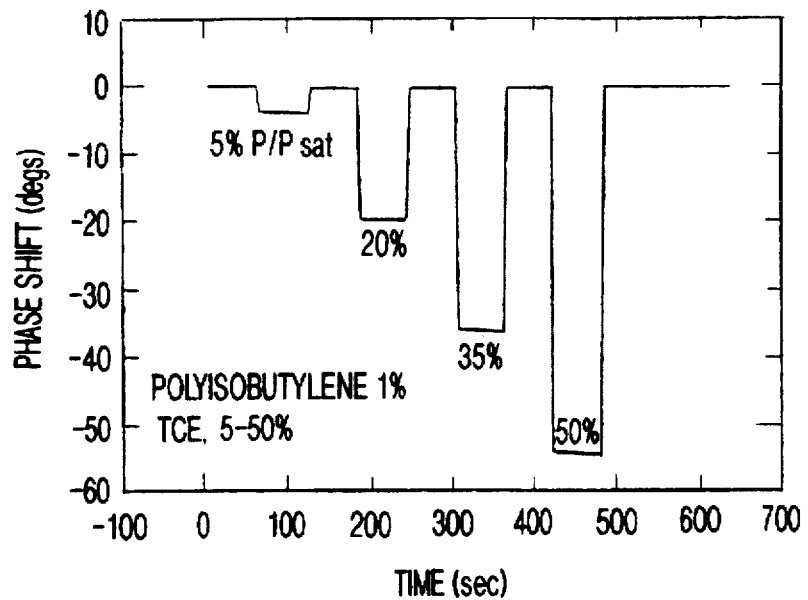
Figure 10B:
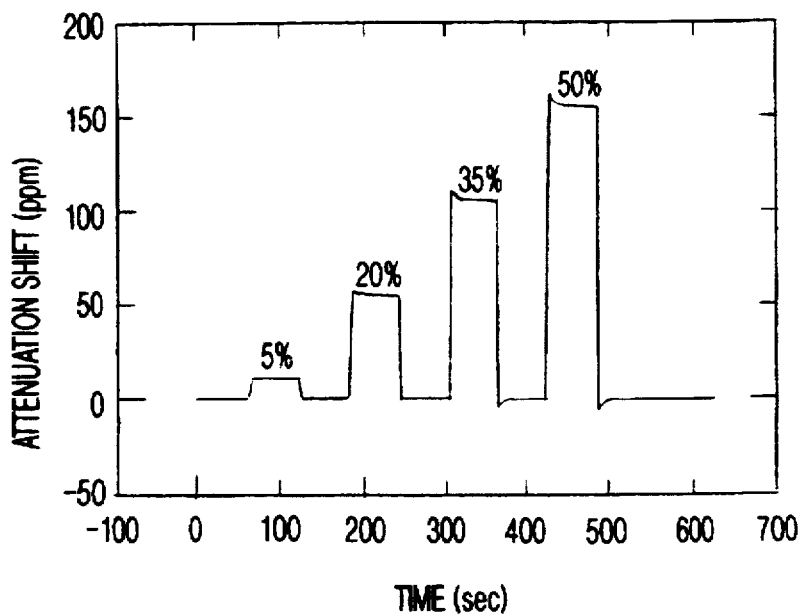
FIG. 10B shows the attenuation shift for the same sequence.

The system described above was used to monitor the concentration of trichloroethylene vapor as a function of time. The concentration was varied in on/off intervals of 1 minute to 5, 20, 35, and 50%P/P$_{sat}$. The sensor response is shown in FIG. 10, FIG. 10A being the phase shift as a function of time and FIG. 10B the attenuation shift as a function of time. Both measurements show clear, sharp response of the sensor system to the change in vapor concentration. When the same sensor was used in this series of measurements using the original oscillator-frequency measurement scheme of Frey and Martin, the large attenuations introduced by the trichloroethylene absorbed onto the polyisobutylene layer were sufficient to cause oscillation in the feedback loop to cease. This emphasizes the advantages of the present sensor phase and amplitude detection system. As oscillation is not required, the measurements could still be made.

The present invention has a very broad scope, with many variations being possible to one skilled in the art. The present invention is intended to be limited only by the claims appended hereto.

We claim:

1. A method for measuring chemical concentrations, comprising mixing the in- and out-of-phase components of a radio-frequency reference signal with a second signal, initially coherent with said reference signal, said second signal having passed through a chemical sensor having an electrical delay time and signal attenuation which depend on chemical concentration, said mixing producing output voltages reflecting the electrical delay time and signal attenuation of said chemical sensor.

2. An apparatus for measuring the chemical environment of chemical sensors, comprising:
   a) a radio-frequency source, having an output port;
   b) a first signal splitter, having an input port connected to the output port of said source and a first and a second signal output port, which divide the first signal splitter input signal in two nominally equal outputs;
   c) a chemical sensor having a sensor input port connected to the first signal output port of said first signal splitter, and a sensor output port;
   d) a second signal splitter, having an input port connected to the sensor output port of said chemical sensor and a first and second signal output port, which divide the second signal splitter input signal into two nominally equal outputs;
   e) a third signal splitter, having an input port connected to the second signal output port of said first signal splitter and a first and a second signal output port, said output ports of the third signal splitter providing outputs substantially equal in average voltage and substantially 90° out of phase with each other;
   f) a first radio-frequency mixer having two input ports, one input port connected to the first signal output port of said second signal splitter and the other input port connected to the first signal output port of said third signal splitter, and an output port delivering a direct-current voltage output $V_1$;
   g) a second radio-frequency mixer having two input ports, one input port connected to the second signal output port of said second signal splitter and the other input port connected to the second signal output port of said third signal splitter, and an output port delivering a direct-current voltage output $V_2$, and;
   h) means for measuring and converting said voltage outputs $V_1$ and $V_2$ into information about the chemical environment of said chemical sensor.

3. The apparatus of claim 2, wherein said chemical sensor comprises a surface-acoustic-wave device.

4. The apparatus of claim 2, wherein said means for measuring and converting comprise a computer-controlled voltmeter and a computer system.

5. An apparatus for measuring the chemical environment of chemical sensors, comprising:
   a) a radio-frequency source having an output port;
   b) a first signal splitter, having an input port connected to the output port of said source and a first and a second signal output port, which divide the first signal splitter input signal in two nominally equal outputs;
   c) a chemical sensor having a sensor input port connected to the first signal output port of said first signal splitter and a sensor output port;
   d) an in-phase and quadrature-phase demodulator, having a local oscillator input port connected to the second signal output port of said first signal splitter, a radio-frequency input port connected to the sensor output port, and first and second output ports which deliver direct-current voltage outputs $V_1$ and $V_2$, respectively, and;
   e) means for measuring and converting said voltage outputs $V_1$ and $V_2$ into information about the chemical environment of said chemical sensor.

6. The apparatus of claim 5, wherein said chemical sensor comprises a surface-acoustic-wave device.

7. The apparatus of claim 5, wherein said means for measuring and converting comprise a computer-controlled voltmeter and a computer system.

8. The apparatus of claim 5, further comprising boosting amplifiers to insure adequate signal level at the local oscillator and radio-frequency input ports of the demodulator.

9. An apparatus for measuring the chemical environment of multiple chemical sensors, comprising:
   a) a radio-frequency source having an output port;
   b) a first signal splitter, having an input port connected to the output port of said source and a first and a second signal output port, which divide the first signal splitter input signal into two nominally equal outputs;
   c) a second signal splitter, having an input port connected to the first signal output port of the first signal splitter and N signal output ports which divide the second signal splitter input signal into N nominally equal outputs;
   d) N chemical sensors, each having a sensor input port connected to a respective signal output port of said first signal splitter and a sensor output port;
   e) a third signal splitter, having an input port connected to the second signal output port of the first signal splitter and N signal output ports which divide the third signal splitter input signal into N nominally equal outputs;
   f) N in-phase and quadrature-phase demodulators, each having a local oscillator input port connected to a respective signal output port of said second signal splitter, a radio-frequency input port connected to a respective sensor output port, and a pair of output ports, each demodulator thereby delivering direct-current voltage outputs $V_1$ and $V_2$, and;
   g) means for measuring and converting said N sets of voltage outputs $V_1$ and $V_2$ into information about the chemical environment of said chemical sensors.

10. The apparatus of claim 9, wherein said N chemical sensors comprise surface-acoustic-wave devices.

11. The apparatus of claim 10, further comprising a reference surface-acoustic-wave device not sensitive to the chemical environment having reference device input and output ports, intercalated in the connection between said second output port of the first signal splitter and said input port of the third signal splitter so that said reference device input port is connected to the second output port of the first signal splitter and said reference device output port is connected to said input port of the third signal splitter.

12. The apparatus of claim 9, wherein said means for measuring and converting comprise a computer-controlled voltmeter, a signal switching system, and a computer system.

13. The apparatus of claim 9, wherein said means for measuring and converting comprises N computer-controlled voltmeters and a computer system.

14. The apparatus of claim 9, wherein said means for measuring and converting comprises a neural net.

15. The apparatus of claim 9, wherein said means for measuring and converting comprises means for pattern recognition.

16. The apparatus of claim 9, further comprising a common test case within which said N chemical sensors are mounted.

17. An apparatus for measuring the chemical environment of multiple chemical sensors, comprising:
   a) a radio-frequency source having an output port;
   b) a first signal splitter, having an input port connected to the output port of said source, a first set of N signal output ports and a second set of N signal output ports, which divide the first signal splitter input signal into 2N nominally equal outputs;
   c) N chemical sensors, each having a sensor input port connected to a respective signal output port from the first set of N signal output ports of said first signal splitter, and a sensor output port;
   d) N in-phase and quadrature-phase demodulators, each having a local oscillator input port connected to a respective signal output port from the second set of N signal output ports of said second signal splitter, a radio-frequency input port connected to a respective sensor output port, and a pair of output ports, each demodulator thereby delivering direct-current voltage outputs $V_1$ and $V_2$, and;
   e) means for measuring and converting said N sets of voltage outputs $V_1$ and $V_2$ into information about the chemical environment of said chemical sensors.

18. The apparatus of claim wherein said N chemical sensors comprise surface-acoustic-wave devices.

19. The apparatus of claim 17, wherein said means for measuring and converting comprise a computer-controlled voltmeter, a signal switching system, and a computer system.

20. The apparatus of claim 17, wherein said means for measuring and converting comprises N computer-controlled voltmeters and a computer system.

21. The apparatus of claim 17, wherein said means for measuring and converting comprises a neural net.

22. The apparatus of claim 17, wherein said means for measuring and converting comprises means for pattern recognition.

23. The apparatus of claim 17, further comprising a common test case within which said N chemical sensors are mounted.

24. An apparatus for measuring the chemical environment of chemical sensors, comprising:
   a) a radio-frequency source having an output port;
   b) a splitter, having a splitter input port connected to said output port of the source and a first and a second splitter output port, which divide the splitter input signal into 2 nominally equal outputs;
   c) a chemical sensor, having a sensor input port connected to the first splitter output port and a sensor output port;
   d) a variable phase shifter, having a reference input port connected to the second splitter output port, a control input port, and a shifted reference output port;
   e) an in-phase and quadrature-phase demodulator, having a radio-frequency input port connected to the sensor output port, a local oscillator input port connected to the shifted reference output port, a first output port and a second output port;
   f) a control feedback circuit, having an input port connected to the second output port of the demodulator and an output port connected to the control input port of the variable phase shifter, and;
   g) means for measuring and converting the voltage at the first output port of the demodulator and the voltage at the control feedback circuit output port into information about the chemical environment of said chemical sensor.

25. The apparatus of claim 24, wherein said chemical sensor comprises a surface-acoustic-wave device.

26. The apparatus of claim 24, wherein said means for measuring and converting comprise a computer-controlled voltmeter and a computer system.

27. An apparatus for measuring the chemical environment of multiple chemical sensors, comprising:
   a) a radio-frequency source having an output port;
   b) a first signal splitter, having an input port connected to the output port of said source and a first and a second signal output port, which divide the first signal splitter input signal into two nominally equal outputs;
   c) a second signal splitter, having an input port connected to the first signal output port of the first signal splitter and N signal output ports which divide the second signal splitter input signal into N nominally equal outputs;
   d) N chemical sensors, each having a sensor input port connected to a respective signal output port of said first signal splitter and a sensor output port;
   e) a third signal splitter, having an input port connected to the second signal output port of the first signal splitter and N signal output ports which divide the third signal splitter input signal into N nominally equal outputs;
   f) N variable phase shifters, each having an input port connected to a respective signal output port of the third signal splitter, a control input port, and a shifted reference signal output port;
   g) N in-phase and quadrature-phase demodulators, each having a local oscillator input port connected to the shifted reference signal output port of a respective variable phase shifter, a radio-frequency input port connected to a respective sensor output port, a first output port, and a second output port;
   h) N control feedback circuits, each having an input port connected to the second output port of a respective demodulator and an output port connected to the control input port of the variable phase shifter whose shifter reference signal output port is connected to the aforementioned demodulator, and;
   i) means for measuring and converting the voltage of the first output port of each demodulator and the voltage at the respective control feedback circuit output port into information about the chemical environment of said chemical sensors.

28. The apparatus of claim 27, wherein N chemical sensors comprise surface-acoustic-wave devices.

29. The apparatus of claim 28, further comprising a reference surface-acoustic-wave device not sensitive to the chemical environment having reference device input and output ports, intercalated in the connection between said second output port of the first signal splitter and said input port of the third signal splitter so that said reference device input port is connected to the second output port of the first signal splitter and said reference device output port is connected to said input port of the third signal splitter.

30. The apparatus of claim 27, wherein said means for measuring and converting comprise a computer-controlled voltmeter, a signal switching system, and a computer system.

31. The apparatus of claim 27, wherein said means for measuring and converting comprises N computer-controlled voltmeters and a computer system.

32. The apparatus of claim 27, wherein said means for measuring and converting comprises a neural net.

33. The apparatus of claim 27, wherein said means for measuring and converting comprises means for pattern recognition.

34. The apparatus of claim 27, further comprising a common test case within which said N chemical sensors are mounted.

35. An apparatus for measuring the chemical environment of chemical sensors, comprising:
   a) a variable frequency source having a control input port and a radio-frequency output port;
   b) a splitter, having a splitter input port connected to said output port of the variable frequency source and a first and a second splitter output port, which divide the splitter input signal into 2 nominally equal outputs;
   c) a chemical sensor, having a sensor input port connected to the first splitter output port and a sensor output port;
   d) an in-phase and quadrature-phase demodulator, having a radio-frequency input port connected to the sensor output port, a local oscillator input port connected the second splitter output port, a first output port and a second output port;
   e) a control feedback circuit, having an input port connected to the second output port of the demodulator and an output port connected to the control input port of the variable frequency source, and;
   f) means for measuring and converting voltages at the first output port of the demodulator and at the control feedback circuit output port into information about the chemical environment of said chemical sensor.

36. The apparatus of claim 35, wherein said chemical sensor comprises a surface-acoustic-wave device.

37. The apparatus of claim 35, wherein said means for measuring and converting comprise a computer-controlled voltmeter and a computer system.

38. The apparatus of claim 35, wherein said control feedback circuit further comprises a gain control.

39. The apparatus of claim 38, wherein said gain control is set to keep the output voltage of the control feedback circuit between nominally ±5 volts.

40. The apparatus of claim 38, wherein the output voltage of the control feedback circuit is a simple multiple of the chemical concentration.

41. The apparatus of claim 35, further comprising zeroing means to set the output voltage of the control feedback circuit to zero when said chemical sensor is not exposed to chemicals to which it is sensitive.

42. The apparatus of claim 35, wherein said means for measuring and converting comprise a voltmeter.

43. The apparatus of claim 35, wherein said means for measuring and converting comprise a variable-gain voltage measuring device.

44. An apparatus for measuring the chemical environment of chemical sensors, comprising:
   a) a radio-frequency source having an output port;
   b) a splitter, having a splitter input port connected to said output port of the source and a first and a second splitter output port, which divide the splitter input signal into 2 nominally equal outputs;
   c) a chemical sensor, having a sensor input port connected to the first splitter output port and a sensor output port;
   d) a variable phase shifter, having a reference input port connected to the second splitter output port, a control input port, and a shifted reference output port;
   e) a mixer with low pass filter having a radio-frequency input port connected to the sensor output port, a local oscillator input port connected to the shifted reference output port, and an intermediate-frequency voltage output port;
   f) a control feedback circuit, having an input port connected to the intermediate frequency voltage output port of the mixer and an output port connected to the control input port of the variable phase shifter, and;
   g) means for measuring and converting a voltage at the control feedback circuit output port into information about the chemical environment of said chemical sensor.

45. The apparatus of claim 44, wherein said chemical sensor comprises a surface-acoustic-wave device.

46. The apparatus of claim 44, wherein said means for measuring and converting comprise a computer-controlled voltmeter and a computer system.

47. The apparatus of claim 44, further comprising boosting amplifiers to insure adequate signal level at the local oscillator and radio-frequency input ports of the mixer.

48. The apparatus of claim 44, wherein said control feedback circuit further comprises a gain control.

49. The apparatus of claim 48, wherein said gain control is set to keep the output voltage of the control feedback circuit between nominally ±5 volts.

50. The apparatus of claim 48, wherein the output voltage of the control feedback circuit is a simple multiple of the chemical concentration.

51. The apparatus of claim 44, further comprising zeroing means for setting the output voltage of the control feedback circuit to zero when said chemical sensor is not exposed to chemicals to which the apparatus is sensitive.

52. The apparatus of claim 44, wherein said means for measuring and converting comprise a voltmeter.

53. The apparatus of claim 44, wherein said means for measuring and converting comprise a variable-gain voltage measuring device.

54. An apparatus for measuring the chemical environment of multiple chemical sensors, comprising:
   a) a radio-frequency source having an output port;
   b) a first signal splitter, having an input port connected to the output port of said source and a first and a second signal output port, which divide the first signal splitter input signal into two nominally equal outputs;
   c) a second signal splitter, having an input port connected to the first signal output port of the first signal splitter and N signal output ports which divide the second signal splitter input signal into N nominally equal outputs;

15 d) N chemical sensors, each having a sensor input port connected to a respective signal output port of said first signal splitter and a sensor output port;

e) a third signal splitter, having an input port connected to the second signal output port of the first signal splitter and N signal output ports which divide the third signal splitter input signal into N nominally equal outputs;

f) N variable phase shifters, each having an input port connected to a respective signal output port of the third signal splitter, a control input port, and a shifted reference signal output port;

g) N mixers, each having a low-pass filter, a local oscillator input port connected to the shifted reference signal output port of a respective variable phase shifter, a radio-frequency input port connected to a respective sensor output port, and an intermediate-frequency voltage output port;

h) N control feedback circuits, each having an input port connected to the intermediate-frequency voltage output port of one of the mixers, and an output port connected to the control input port of the variable phase shifter whose shifter reference signal output port is connected to the aforementioned mixer, and;

i) means for measuring and converting voltages at the control feedback circuit output ports into information about the chemical environment of said chemical sensors.

55. The apparatus of claim 54, wherein said N chemical sensors comprise surface-acoustic-wave devices.

56. The apparatus of claim 55, further comprising a reference surface-acoustic-wave device not sensitive to the chemical environment having reference device input and output ports, intercalated in the connection between said second output port of the first signal splitter and said input port of the third signal splitter so that said reference device input port is connected to the second output port of the first signal splitter and said reference device output port is connected to said input port of the third signal splitter.

57. The apparatus of claim 54, wherein said means for measuring and converting comprise a computer-controlled voltmeter, a signal switching system, and a computer system.

58. The apparatus of claim 54, wherein said means for measuring and converting comprises N computer-controlled voltmeters and a computer system.

59. The apparatus of claim 54, wherein said means for measuring and converting comprises a neural net.

60. The apparatus of claim 54, wherein said means for measuring and converting comprises means for pattern recognition.

61. The apparatus of claim 54, further comprising a common test case within which said N chemical sensors are housed.

62. The apparatus of claim 54, wherein said control feedback circuits further comprise gain controls.

63. The apparatus of claim 62, wherein said gain controls keep the output voltage of each control feedback circuit between nominally ±5 volts.

64. The apparatus of claim 62, wherein the output voltages of the control feedback circuits are a simple multiple of the chemical concentration.

65. The apparatus of claim 54, further comprising zeroing means to set the output voltages of the control feedback circuits to zero when said chemical sensors are not exposed to chemicals to which they are sensitive.

66. The apparatus of claim 54, wherein said means for measuring and converting comprise a voltmeter.

16

67. The apparatus of claim 54, wherein said means for measuring and converting comprise a variable-gain measuring device.

68. An apparatus for measuring the chemical environment of chemical sensors, comprising:

a) a variable frequency source having a control input port and a radio-frequency output port;

b) a splitter, having a splitter input port connected to said output port of the variable frequency source and a first and a second splitter output port, which divide the splitter input signal into 2 nominally equal outputs;

c) a chemical sensor, having a sensor input port connected to the first splitter output port and a sensor output port;

d) a mixer with low-pass filter, having a radio-frequency input port connected to the sensor output port, a local oscillator input port connected to the second splitter output port, and an intermediate-frequency voltage output port;

e) a control feedback circuit, having an input port connected to the intermediate-frequency voltage output port of the mixer and an output port connected to the control input port of the variable frequency source, and;

f) means for measuring and converting a voltage at the control feedback circuit output port into information about the chemical environment of said chemical sensor.

69. The apparatus of claim 68, wherein said chemical sensor comprises a surface-acoustic-wave device.

70. The apparatus of claim 68, wherein said means for measuring and converting comprise a computer-controlled voltmeter and a computer system.

71. The apparatus of claim 68, further comprising boosting amplifiers to insure adequate signal level at the local oscillator and radio-frequency input ports of the mixer.

72. The apparatus of claim 68, wherein said control feedback circuit further comprises a gain control.

73. The apparatus of claim 72, wherein said gain control is set to keep the output voltage of the control feedback circuit between nominally ±5 volts.

74. The apparatus of claim 72, wherein the output voltage of the control feedback circuit is a simple multiple of the chemical concentration.

75. The apparatus of claim 68, further comprising zeroing means for setting the output voltage of the control feedback circuit to zero when said chemical sensor is not exposed to chemicals to which the apparatus is sensitive.

76. The apparatus of claim 68, wherein said means for measuring and converting comprise a voltmeter.

77. The apparatus of claim 68, wherein said means for measuring and converting comprise a variable-gain voltage measuring device.

78. An apparatus for measuring the chemical environment of chemical sensors, comprising:

a) a radio-frequency source having an output port;

b) a first splitter, having a first splitter input port connected to said output port of the source and a pair of first splitter output ports, which divide a first splitter input signal into 2 nominally equal outputs;

c) a chemical sensor, having a sensor input port connected to one of the pair of first splitter output ports and a sensor output port;

d) a second splitter, having a second splitter input port connected to said sensor output port and a pair of second splitter output ports, which divide a second splitter input signal into 2 nominally equal outputs;

e) a radio-frequency power detector, having a detector input port connected to another of the pair of second splitter output ports and a detector output port providing an attenuation response of the chemical sensor;

f) a variable phase shifter, having a reference input port connected to one of the pair of first splitter output ports, a control input port, and a shifted reference output port;

g) a mixer with low pass filter having a radio-frequency input port connected to another of the pair of second splitter output ports, a local oscillator input port connected to the shifted reference output port of the variable phase shifter, and an intermediate-frequency voltage output port;

h) a control feedback circuit, having an input port connected to the intermediate-frequency voltage output port of the mixer and an output port connected to the control input port of the variable phase shifter to provide a voltage thereto, and;

i) means for measuring and converting the voltage at the control feedback circuit output port and the voltage at the radio-frequency power detector output port into information about the chemical environment of said chemical sensor.

79. The apparatus of claim 78, wherein said chemical sensor comprises a surface-acoustic-wave device.

80. The apparatus of claim 78, wherein said means for measuring and converting comprise a computer-controlled voltmeter and a computer system.

81. The apparatus of claim 78, wherein said control feedback circuit further comprises a gain control.

82. The apparatus of claim 81, wherein said gain control is set to keep the output voltage of the control feedback circuit between nominally ±5 volts.

83. The apparatus of claim 81, wherein the output voltage of the control feedback circuit is a simple multiple of the chemical concentration.

84. The apparatus of claim 78, further comprising zeroing means for setting the output voltage of the control feedback to zero when said chemical sensor is not exposed to chemicals to which the apparatus is sensitive.

85. The apparatus of claim 78, wherein said means for measuring and converting comprise a voltmeter.

86. The apparatus of claim 78, wherein said means for measuring and converting comprise a variable-gain voltage measuring device.

87. An apparatus for measuring the chemical environment of chemical sensors, comprising:

a) a variable frequency source having a control input port and a radio-frequency output port;

b) a first splitter, having a first splitter input port connected to said output port of the variable frequency source and a pair of first splitter output ports, which divide a first splitter input signal into 2 nominally equal outputs;

c) a chemical sensor, having a sensor input port connected to one of the pair of first splitter output ports and a sensor output port;

d) a second splitter, having a second splitter input port connected to the sensor output port and a pair of second splitter output ports, which divide a second splitter input signal into 2 nominally equal outputs;

e) a radio-frequency power detector, having a detector input port connected to one of the pair of second splitter output ports and a detector output port providing an attenuation response of the chemical sensor;

f) a mixer with a low-pass filter, having a radio-frequency input port connected to another of the pair of second splitter output ports, a local oscillator input port connected to another of the pair of first splitter output ports, and an intermediate-frequency voltage output port;

g) a control feedback circuit, having an input port connected to the intermediate-frequency voltage output port of the mixer and an output port connected to the control input port of the variable frequency source, and;

h) means for measuring and converting the voltage at the control feedback circuit output port and the voltage at the detector output port into information about the chemical environment of said chemical sensor.

88. The apparatus of claim 87, wherein said chemical sensor comprises a surface-acoustic-wave device.

89. The apparatus of claim 87, wherein said means for measuring and converting comprise a computer-controlled voltmeter and a computer system.

90. The apparatus of claim 87, wherein said control feedback circuit further comprises a gain control.

91. The apparatus of claim 90, wherein said gain control is set to keep the output voltage of the control feedback circuit between nominally ±5 volts.

92. The apparatus of claim 90 wherein the output voltage of the control feedback circuit is a simple multiple of the chemical concentration.

93. The apparatus of claim 90, further comprising zeroing means for setting the output voltage of the control feedback circuit to zero when said chemical sensor is not exposed to chemicals to which the apparatus is sensitive.

94. The apparatus of claim 87, wherein said means for measuring and converting comprise a voltmeter.

95. The apparatus of claim 87, wherein said means for measuring and converting comprise a variable-gain voltage measuring device.

96. An apparatus for measuring the chemical environment of at least one chemical sensor, comprising:

a) a source connected to an input port of each sensor for activation thereof at a radio frequency; and b) detection means, including an in-phase and quadrature-phase demodulator, connected to the source and to an output port of each chemical sensor for providing a pair of output voltages with each output voltage being proportional to a difference in phase between the input and output ports of each chemical sensor for determining information about the chemical environment.

97. The apparatus of claim 96, wherein each chemical sensor is a surface-acoustic-wave sensor.

98. The apparatus of claim 96, wherein the detection means further includes amplifier means connected to at least one input of the demodulator for insuring an adequate signal level thereat.

99. The apparatus of claim 96, wherein the detection means further includes feedback means for providing a substantially constant quadrature-phase signal from the demodulator.

100. The apparatus of claim 96, further comprising a reference sensor isolated from the chemical environment and providing a reference signal to the detection means.

101. The apparatus of claim 96, wherein each output voltage is further proportional to a product of amplitudes of a local oscillator input and a radio-frequency input provided to the demodulator.

102. The apparatus of claim 96, further comprising computing means for extracting phase and amplitude shifts from the pair of output voltages.

* * * * *